United States Patent

Ohi et al.

Patent Number: 5,567,825
Date of Patent: Oct. 22, 1996

[54] METHOD FOR THE PREPARATION OF A TRIAZOLE COMPOUND

[75] Inventors: Hideo Ohi; Noriyuki Ozawa, both of Shizuoka-ken, Japan

[73] Assignees: Chugai Seiyaku Kabushiki Kaisha; Ihara Chemical Industry Co., Ltd., both of Tokyo, Japan

[21] Appl. No.: 577,878

[22] Filed: Dec. 22, 1995

[30] Foreign Application Priority Data

Dec. 22, 1994 [JP] Japan .................. 6-320865

[51] Int. Cl.$^6$ ........................................ C07D 249/12
[52] U.S. Cl. ........................................ 548/264.2
[58] Field of Search ............................. 548/264.2

[56] References Cited

U.S. PATENT DOCUMENTS 3,119,877  1/1964  Campbell et al. .
5,338,720  8/1994  Takeuchi et al. .............. 548/264.2

FOREIGN PATENT DOCUMENTS 0332133  9/1989  European Pat. Off. .

OTHER PUBLICATIONS

*Chemical Abstracts,* vol. 121, No. 7, p. 1175, abstract No. 205358m(abstract of JP-A-06 080 651) (1994).
*Chemical Abstracts,* vol. 111, No. 25, p. 789, abstract No. 232788b (abstract of JP-A-01 121 279) (1989).

*Methoden der Organischen Chemie, (Houben–Weyl), Band E11, Organische Schwefel–Verbindungen,* Georg Thiem Verlag (Stuttgart), p. 174 (1985).
M. Fieser, *Fieser and Fieser's Reagents for Organic Synthesis,* vol. 11, Wiley–Interscience (New York), pp. 202–203 (1974).

*Primary Examiner*—Patricia L. Morris
*Attorney, Agent, or Firm*—Wenderoth, Lind & Ponack

[57] ABSTRACT

The improvement proposed in the invention consists in the use of, as a reaction solvent in the reaction of a 1,3,5-trialkyl-2-halogenobenzene and an alkali metal salt of 3-mercapto-1H-1,2,4-triazole in the presence of a copper catalyst for the preparation of a 3-(2,4,6-trialkylphenylthio)-1H-1,2,4-triazole useful as an intermediate in the preparation of herbicide compounds, a compound represented by the general formula

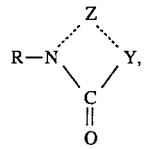

in which R is a lower alkyl group, Y is a methylene group or an N-(lower alkyl)imino group and Z is a divalent hydrocarbon group to form a 5-membered ring or 6-membered ring together with the group —N—CO—Y—, such as N-methyl-2-pyrrolidone, N,N'-dimethyl-2-imidazolidinone and N,N'-dimethyl propylene urea, so as to obtain the product in a high yield without the danger of explosion.

5 Claims, No Drawings

METHOD FOR THE PREPARATION OF A TRIAZOLE COMPOUND

BACKGROUND OF THE INVENTION

The present invention relates to a method for the preparation of a specific triazole compound. More particularly, the invention relates to a novel and efficient industrial method for the preparation of a triazole compound or, in particular, a 3-(2,4,6-trialkylphenylthio)-1H-1,2,4-triazole compound, which is useful as an intermediate in the synthetic preparation of various kinds of carbamoyl triazole-based herbicides.

As is well known, some of carbamoyl triazole derivatives have excellent herbicidal activity so that active investigations are now under way for the development of herbicides containing such a compound as the effective ingredient.

While the above mentioned carbamoyl triazole derivatives can be synthesized from a triazole derivative having an alkyl-substituted phenyl sulfide group as an intermediate, various methods have been proposed heretofore for the synthetic preparation of these intermediate compounds. For example, Japanese Patent Publication 5-73745 discloses a synthetic route via a diazonium salt starting from amino mesitylene. This method, however, is far from satisfactory as an industrial method because the yield of the product compound can rarely exceed 50% and the reaction for the preparation of the diazonium compound involves troublesome procedures if not to mention the risk of explosion in the reaction as is taught in guide books for organic syntheses that the reaction of an aromatic diazonium salt and a thiol compound involves an explosive decomposition of the diazo sulfide.

On the other hand, Japanese Patent Kokai 1-121279 proposes a method in which a triazole compound is obtained by the reaction of 3-mercapto-1H-1,2,4-triazole and a halogenobenzene unsubstituted or substituted by one or two of substituent groups selected from nitro group and trifluoromethyl group in the presence of a base. An experiment is disclosed therein according to which a reaction was performed by using 3,5-bis(trifluoromethyl) bromobenzene in the presence of a catalytic amount of copper (I) chloride in N,N-dimethylformamide as the solvent. As being motivated by this disclosure, the inventors conducted an experiment on an assumption that the reaction with a 1,3,5-trialkyl-2-halogenobenzene could hopefully proceed under similar conditions to obtain a result that the desired triazole compound could hardly be obtained in contrast to the above mentioned assumption.

The reason therefor is presumably that, when an electron-attractive group such as trifluoromethyl group or nitro group is introduced into the benzene nucleus, elimination of the halogen atom from the benzene nucleus readily proceeds to promote proceeding of the reaction so that the desired triazole compound can be obtained even by the use of N,N-dimethylformamide as the solvent while, when three lower alkyl groups as electron-donating groups are introduced into the benzene nucleus as in a 1,3,5-trialkyl-2-halogenobenzene, elimination of the halogen atom from the benzene nucleus is prevented to cause retardation of the reaction so that the desired triazole compound cannot be obtained by using N,N-dimethylformamide as the solvent.

SUMMARY OF THE INVENTION

The present invention has an object to provide, by overcoming the above described problems and disadvantages in the prior art methods, a novel and efficient industrial method for the preparation of a specific triazole-based compound having usefulness as an intermediate in the preparation of a carbamoyl triazole-based herbicide in a simple and convenient procedure without the danger of explosion. The guide principle leading to the present invention is that, according to the extensive investigations on the reaction between a 1,3,5-trialkyl-2-halogenobenzene and an alkali metal salt of 3-mercapto-1H-1,2,4-triazole in the presence of a copper catalyst, a key factor to promote the reaction is in the selection of the reaction solvent and the desired triazole compound can be efficiently obtained by the proper selection of the solvent.

Thus, the present invention provides an improvement, in the synthetic method for the preparation of a 3-(2,4,6-trialkylphenylthio)-1H-1,2,4-triazole compound represented by the general formula

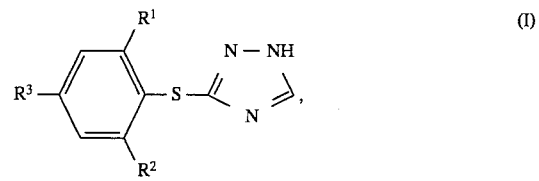

in which $R^1$, $R^2$ and $R^3$ are each, independently from the others, a lower alkyl group, by the reaction between a 1,3,5-trialkyl-2-halogenobenzene represented by the general formula

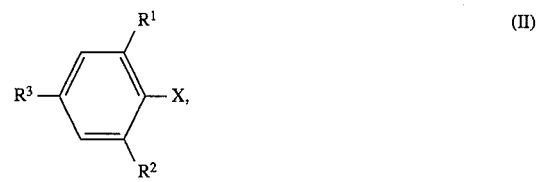

in which $R^1$, $R^2$ and $R^3$ each have the same meaning as defined above and X is a halogen atom, and an alkali metal salt of 3-mercapto-1H-1,2,4-triazole in the presence of a copper catalyst, which comprises conducting the reaction in an organic compound as a solvent represented by the general formula

in which R is a lower alkyl group, Y is a methylene group or an N-(lower alkyl)imino group and Z is a divalent hydrocarbon group to form a 5-membered ring or 6-membered ring together with the group —N—CO—Y—.

DETAILED DESCRIPTION OF THE PREFERRED EMBODIMENTS

One of the starting reactants used in the reaction according to the present invention is a 1,3,5-trialkyl-2-halogenobenzene represented by the general formula

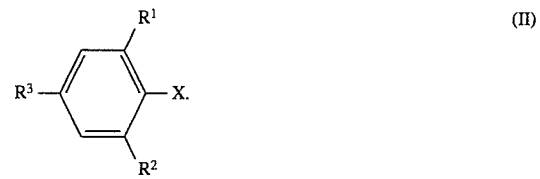

In the general formula $R^1$, $R^2$ and $R^3$ are each, independently from the others, a lower alkyl group having 1 to 6 carbon atoms exemplified by methyl, ethyl, propyl, butyl, pentyl and hexyl groups. Although these alkyl groups are not limited to straightly linear ones but can be branched or cyclic ones, it is preferable that the alkyl group is a straightly linear alkyl group having 1 to 4 carbon atoms including methyl, ethyl, n-propyl and n-butyl groups in respect of the reaction velocity and the yield of the desired product. X in the general formula is an atom of halogen which is preferably bromine or iodine in respect of the reaction velocity and the yield of the desired product.

Examples of preferable 1,3,5-trialkyl-2-halogenobenzene compounds represented by the general formula (II) include bromomesitylene, iodomesitylene, 2-bromo-1,3,5-triethylbenzene, 1,3,5-triethyl-2-iodobenzene, 2-bromo-1,3 -dimethyl-5-ethylbenzene, 1,3-dimethyl-5-ethyl-2-iodobenzene, 2-bromo-1,3-diethyl-5-methylbenzene, 1,3-diethyl-5-methyl-2-iodobenzene, 2-bromo-1,5-dimethyl-3-ethylbenzene, 1,5 -dimethyl-3-ethyl-2-iodobenzene, 2-bromo-1,5-diethyl-3-methylbenzene, 1,5-diethyl-3-methyl-2-iodobenzene and the like.

The above mentioned 1,3,5-trialkyl-2-halogenobenzene compound can be prepared by several known synthetic methods and usable without particular limitations relative to the synthetic method. For example, the compound can be prepared by the halogenation reaction of a corresponding 1,3,5-trialkyl benzene in a known procedure.

The other reactant in the inventive method to be reacted with the 1,3,5-trialkyl-2-halogeno benzene is a salt of an alkali metal, i.e. lithium, sodium, potassium, rubidium or cesium, of 3-mercapto-1H-1,2,4-triazole, of which sodium salt and potassium salt are preferable in respect of their inexpensiveness.

The amount of the above mentioned alkali metal salt of 3-mercapto-1H-1,2,4-triazole used in the inventive reaction is selected in the range from 1.0 to 1.5 moles or, preferably, from 1.0 to 1.1 moles per mole of the 1,3,5-trialkyl-2-halogenobenzene. This alkali metal salt can be used in the form of the salt as prepared in advance or, alternatively, can pertain to the reaction as formed in situ in the reaction mixture as is described later.

The alkali metal salt of 3-mercapto-1H-1,2,4-triazole can be prepared in the following manner. Thus, 3-mercapto-1H-1,2,4-triazole and an alkali metal or an alkali metal hydroxide are added to an alcoholic solvent and the reaction mixture is heated under reflux followed by removal of the alcoholic solvent and water formed by the reaction. Suitable alcoholic solvent includes methyl and ethyl alcohols. When the alkali metal salt of 3-mercapto-1H-1,2,4-triazole is to be formed in situ in the reaction mixture from 3-mercapto-1H-1,2,4-triazole and a basic compound, the basic compound is selected from inorganic compounds of an alkali metal such as hydroxides, carbonates, hydrides and the like. Preferable basic compounds include sodium hydroxide, potassium hydroxide, sodium carbonate, potassium carbonate and sodium hydride. The amount of the basic compound used in the in situ formation of the alkali metal salt is in the range from 1.0 to 2.5 moles or, preferably, from 1.0 to 2.0 moles or, more preferably, from 1.0 to 1.5 moles per mole of the mercapto compound. 3-Mercapto-1H-1,2,4-triazole is a known compound and can be readily prepared by the synthetic method described in many literatures.

In the synthetic method according to the invention, the above described two reactants are reacted in the presence of a copper compound as a catalyst. Suitable copper compounds include copper (I) salts or, in particular, copper (I) halides such as copper (I) chloride, copper (I) bromide and copper (I) iodide, oxides of copper such as copper (I) oxide and metallic copper, of which monovalent copper salts such as copper (I) halides are preferable in respect of the high yield of the desired product and inexpensiveness. These copper compounds can be used as the catalyst either singly or as a combination of two kinds or more according to need. The amount of the copper compound used in the inventive reaction as a catalyst is in the range from 0.005 to 0.3 mole or, preferably, from 0.007 to 0.2 mole per mole of the 1,3,5-trialkyl-2-halogenobenzene.

The most characteristic feature in the inventive method is the use of a specific compound as the reaction solvent. The solvent compound is represented by the general formula

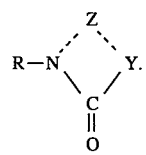 (III)

In the above given general formula, R is a lower alkyl group having 1 to 4 carbon atoms such as methyl, ethyl, n-propyl and isopropyl groups. Y in the general formula is a methylene group or a lower-alkylimino group such as N-methylimino, N-ethylimino, N-n-propylimino and N-isopropylimino groups. Z in the general formula is a divalent hydrocarbon group which forms a 5-membered ring or 6-membered ring structure together with the group —N—CO—Y—.

Examples of the solvent compound represented by the above given general formula include N-(lower alkyl)-2-pyrrolidones such as N-methyl-2-pyrrolidone, N-ethyl-2-pyrrolidone, N-n-propyl-2-pyrrolidone, N-isopropyl-2-pyrrolidone and the like, N,N'-di(lower alkyl)-2-imidazolidinones such as N,N'-dimethyl-2-imidazolidinone, N,N'-diethyl-2-imidazolidinone, N,N'-di-n-propyl-2-imidazolidinone, N,N'-diisopropyl-2-imidazolidinone, N-methyl-N'-ethyl-2-imidazolidinone, N-methyl-N'-n-propyl-2-imidazolidinone, N-methyl-N'-isopropyl-2-imidazolidinone, N-ethyl-N'-n-propyl-2-imidazolidinone, N-ethyl-N'-isopropyl-2-imidazolidinone and the like among the compounds having a 5-membered ring structure and N-(lower alkyl)-2-piperidones such as N-methyl-2-piperidone, N-ethyl-2-piperidone, N-n-propyl-2-piperidone, N-isopropyl-2-piperidone and the like, N,N'-di(lower alkyl) propylene ureas such as N,N'-dimethyl propylene urea, N,N'-diethyl propylene urea, N,N'-di-n-propyl propylene urea, N,N'-diisopropyl propylene urea, N-methyl-N'-ethyl propylene urea, N-methyl-N'-n-propyl propylene urea, N-methyl-N'-isopropyl propylene urea, N-ethyl-N'-n-propyl propylene urea, N-ethyl-N'-isopropyl propylene urea and the like among the compounds having a 6-membered ring structure, of which N-methyl-2-pyrrolidone, N,N'-dimethyl-2-imidazolidinone and N,N'-dimethyl propylene urea are particularly preferable.

These solvent compounds can be used either singly or as a mixture of two kinds or more according to need in any mixing proportions without particular limitations. The solvent used in the inventive reaction can be a mixture of the above specified solvent compound or compounds and one or more of other inert solvents in a limited proportion of, for example, 10% by volume or smaller. Examples of such an inert solvent include aromatic hydrocarbon compounds such as benzene, toluene, xylene and ethyl benzene.

The amount of the reaction solvent, which can be the above specified solvent compound or a mixture thereof with other inert solvents, used in the inventive reaction is, though not particularly limited provided that the reaction mixture has a consistency suitable for agitation, in the range from 0.1 to 2 liters or, preferably, from 0.25 to 1.0 liter per mole of the 1,3,5-trialkyl-2-halogenobenzene as one of the reactants.

The reaction mixture prepared in the above described formulation is heated at a temperature of 150° C. or higher or, preferably, in the range from 170° to 210° C. in order to promote the reaction. When the reaction temperature is too high, a disadvantage is caused due to predominance of undesirable side reactions. Though dependent on various factors such as kinds of the reactant compounds, kind and amount of the catalytic compound, kind of the solvent compound, reaction temperature and others, the reaction of the invention is complete usually within 1 to 24 hours to give the desired triazole compound of the general formula (I) in a good yield without the problems of explosion or decomposition of the solvent as are unavoidable in the prior art methods.

The triazole compound of the general formula (I) as the product of the inventive method can be converted by the method disclosed in, for example, Japanese Patent Publication 5-73745 to a compound which serves as an effective ingredient in a triazole-based herbicide according to the following reaction scheme:

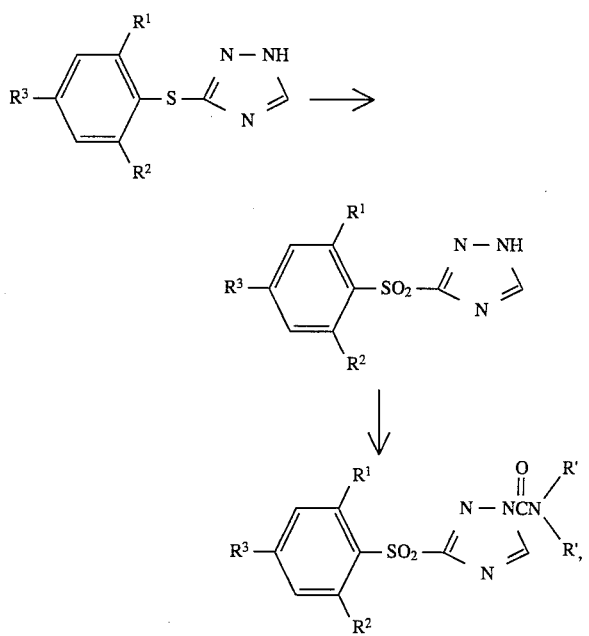

in which R' is an alkyl group and $R^1$, $R^2$ and $R^3$ each have the same meaning as defined before.

In the following, the present invention is described in more detail by way of examples, which, however, never limit the scope of the invention in any way.

EXAMPLE 1

Into a flask of 250 ml capacity equipped with a thermometer, reflux condenser and stirrer were introduced 40 g (0.20 mole) of bromomesitylene, 24.6 g (0.20 mole) of sodium salt of 3-mercapto-1H-1,2,4-triazole, 100 ml of N,N'-dimethyl-2-imidazolidinone, referred to as DMI hereinafter, and 0.25 g (0.0017 mole) of copper (I) oxide $Cu_2O$ to form a reaction mixture which was heated at 190° C. for 9 hours. After cooling to room temperature, the reaction mixture was poured into ice water and the insoluble matter was removed by filtration. The filtrate was adjusted to neutrality to acidity by the addition of diluted hydrochloric acid to precipitate a solid matter which was collected by filtration and again dissolved in ethyl acetate followed by removal of the insoluble matter by filtration. The filtrate was subjected to distillation to remove ethyl acetate leaving 32.9 g of a colorless crystal as the product having a melting point of 188° to 190° C., which could be identified to be 3-(2,4,6-trimethylphenylthio)-1H-1,2,4-triazole. The above mentioned yield of the product corresponds to 75% of the theoretical value.

The sodium salt of 3-mercapto-1H-1,2,4-triazole used as a reactant in the above described procedure was a product obtained in advance by heating a reaction mixture of 3-mercapto-1H-1,2,4-triazole and sodium hydroxide in ethyl alcohol under reflux for 1 hour followed by removal of ethyl alcohol and water formed by the reaction by distillation under reduced pressure.

EXAMPLE 2

Into a flask of 250 ml capacity equipped with a thermometer, reflux condenser and stirrer were introduced 40 g (0.20 mole) of bromomesitylene, 20 g (0.20 mole) of 3-mercapto-1H-1,2,4-triazole, 100 ml of DMI, 21 g (0.20 mole) of sodium carbonate and 0.25 g (0.0017 mole) of copper (I) oxide $Cu_2O$ to form a reaction mixture which was heated at 190° to 200° C. Eor 9 hours while water formed by the reaction was continuously removed out of the reaction mixture. After cooling to room temperature, the reaction mixture was poured into ice water and the insoluble matter was removed by filtration. The filtrate was adjusted to neutrality to acidity by the addition of diluted hydrochloric acid to precipitate a solid matter which was collected by filtration and again dissolved in ethyl acetate followed by removal of the insoluble matter by filtration. The filtrate was subjected to distillation to remove ethyl acetate leaving 34.1 g of a colorless crystal as the product having a melting point of 188° to 190° C., which could be identified to be 3-(2,4,6-trimethylphenylthio)-1H-1,2,4-triazole. The above mentioned yield of the product corresponds to 79% of the theoretical value.

EXAMPLE 3

The experimental procedure for the preparation of 3-(2,4,6-trimethylphenylthio)-1H-1,2,4-triazole was substantially the same as in Example 2 except that the amount of sodium carbonate was increased to 0.21 mole, the amount of copper (I) oxide was increased to 0.0040 mole and the reaction was terminated after 8 hours of heating of the reaction mixture. The yield of the product was 71.0% of the theoretical value.

EXAMPLE 4

The experimental procedure for the preparation of 3-(2,4,6-trimethylphenylthio)-1H-1,2,4-triazole was substantially the same as in Example 3 except that the copper (I) oxide was replaced with 0.0040 mole of copper (I) iodide and the reaction time was extended to 10 hours. The yield of the product was 80.1% of the theoretical value.

EXAMPLE 5

The experimental procedure for the preparation of 3-(2,4,6-trimethylphenylthio)-1H-1,2,4-triazole was substantially the same as in Example 3 except that DMI as the reaction solvent was replaced with the same volume of N-methyl-2-pyrrolidone and the reaction time was extended to 10 hours. The yield of the product was 76.8% of the theoretical value.

EXAMPLE 6

The experimental procedure for the preparation of 3-(2, 4,6-trimethylphenylthio)-1H-1,2,4-triazole was substantially the same as in Example 3 except that DMI as the reaction solvent was replaced with the same volume of N,N'-dimethyl propylene urea, the amount of copper (I) oxide was increased to 0.0060 mole, the reaction temperature was controlled in the range from 190° to 193° C. and the reaction time was extended to 9 hours. The yield of the product was 73.1% of the theoretical value.

EXAMPLE 7

The experimental procedure for the preparation of 3-(2, 4,6-trimethylphenylthio)-1H-1,2,4-triazole was substantially the same as in Example 3 except that sodium carbonate was replaced with 0.20 mole of potassium hydroxide, the amount of copper (I) oxide was decreased to 0.0020 mole, the reaction temperature was controlled in the range from 190° to 193° C. and the reaction was terminated after 7 hours. The yield of the product was 73.4% of the theoretical value.

EXAMPLE 8

The experimental procedure for the preparation of 3-(2, 4,6-trimethylphenylthio)-1H-1,2,4-triazole was substantially the same as in Example 3 except that the amount of the sodium carbonate was decreased to 0.20 mole, the amount of copper (I) oxide was decreased to 0.0020 mole, the reaction temperature was constant at about 170° C. and the reaction was terminated after 7 hours. The yield of the product was 66.7% of the theoretical value.

EXAMPLE 9

The experimental procedure for the preparation of 3-(2, 4,6-trimethylphenylthio)-1H-1,2,4-triazole was substantially the same as in Example 3 except that the copper (I) oxide was replaced with 0.0040 mole of metallic copper dust and the reaction time was extended to 10 hours. The yield of the product was 67.2% of the theoretical value.

EXAMPLE 10

The experimental procedure for the preparation of 3-(2, 4,6-trimethylphenylthio)-1H-1,2,4-triazole was substantially the same as in Example 2 except that bromomesitylene was replaced with 50.0 g (0.20 mole) of iodomesitylene and the reaction time was decreased to 4 hours. The yield of the product was 37.1 g corresponding to 86.0% of the theoretical value.

Comparative Example 1

The experimental procedure was substantially the same as in Example 2 excepting replacement of DMI with the same volume (100 ml) of N,N-dimethylformamide. After 9 hours of heating of the reaction mixture, a small portion of the reaction mixture was taken and gas-chromatographically analyzed to find that the desired 3-(2,4,6-trimethylphenylthio)- 1H-1,2,4-triazole was contained therein only in a trace amount. In addition, the reaction mixture emitted unpleasant odor presumably due to decomposition of the N,N-dimethylformamide.

Comparative Example 2

The experimental procedure was substantially the same as in Example 2 except that DMI was replaced with the same volume of dimethylsulfoxide, the amount of sodium carbonate was increased to 0.21 mole, the amount of copper (I) oxide was increased to 0.0060 mole and the reaction mixture was heated at about 185° C. under reflux for 15 hours. The result was that the desired product could be obtained only in a trace amount.

Comparative Example 3

The experimental procedure was substantially the same as in Example 2 except that DMI was replaced with the same volume of N,N-dimethylacetamide, the amount of sodium carbonate was increased to 0.21 mole, the amount of copper (I) oxide was increased to 0.0020 mole and the reaction mixture was heated at about 165° C. under reflux for 15 hours. The result was that the desired product could be obtained only in a trace amount.

What is claimed is:

1. In a synthetic method for the preparation of a 3-( 2,4,6-trialkylphenylthio)-1H-1,2,4-triazole compound represented by the general formula

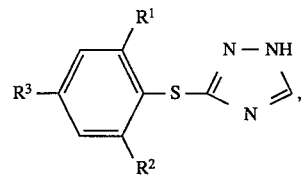

in which $R^1$, $R^2$ and $R^3$ are each, independently from the others, a lower alkyl group, by the reaction between a 1,3,5-trialkyl-2-halogenobenzene represented by the general formula

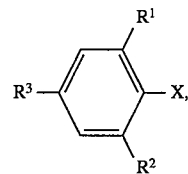

in which $R^1$, $R^2$ and $R^3$ each have the same meaning as defined above and X is a halogen atom, and an alkali metal salt of 3-mercapto-1H-1,2,4-triazole in the presence of a copper catalyst, the improvement which comprises conducting the reaction in an organic compound as a solvent represented by the general formula

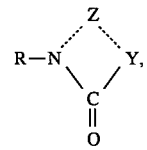

in which R is a lower alkyl group, Y is a methylene group or an N-(lower alkyl)imino group and Z is a divalent hydrocarbon group to form a 5-membered ring or 6-membered ring together with the group —N—CO—Y—.

2. The improvement as claimed in claim 1 in which the alkyl group denoted by R is selected from the group consisting of methyl group, ethyl group, n-propyl group and isopropyl group.

3. The improvement as claimed in claim 1 in which the (lower alkyl)imino group denoted by Y is selected from the group consisting of N-methylimino group, N-ethylimino group, N-n-propylimino group and N-isopropylimino group.

4. The improvement as claimed in claim 1 in which the organic compound as a solvent is selected from the group consisting of N-methyl-2-pyrrolidone, N,N'-dimethyl-2-imidazolidinone and N,N'-dimethyl propylene urea.

5. The improvement as claimed in claim 1 in which the amount of the organic compound as a solvent is in the range from 0.1 to 2.0 liters per mole of the 1,3,5-trialkyl-2-halogenobenzene.

* * * * *